(12) United States Patent
Reeves et al.

(10) Patent No.: US 11,903,346 B2
(45) Date of Patent: *Feb. 20, 2024

(54) PERENNIAL MONOCOTYLEDON GRAFTING

(71) Applicant: CAMBRIDGE ENTERPRISE LIMITED, Cambridge (GB)

(72) Inventors: Gregory Reeves, Cambridge (GB); Julian Hibberd, Cambridge (GB)

(73) Assignee: CAMBRIDGE ENTERPRISE LIMITED, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/293,865

(22) PCT Filed: Nov. 14, 2019

(86) PCT No.: PCT/GB2019/053232
§ 371 (c)(1),
(2) Date: May 13, 2021

(87) PCT Pub. No.: WO2020/099879
PCT Pub. Date: May 22, 2020

(65) Prior Publication Data
US 2022/0007588 A1    Jan. 13, 2022

(30) Foreign Application Priority Data

Nov. 14, 2018   (GB) ..................... 1818578

(51) Int. Cl.
*A01G 2/30* (2018.01)
*A01H 4/00* (2006.01)

(52) U.S. Cl.
CPC ............... *A01G 2/30* (2018.02); *A01H 4/005* (2013.01)

(58) Field of Classification Search
CPC .................................. A01G 2/30; A01G 2/35
See application file for complete search history.

(56) References Cited

U.S. PATENT DOCUMENTS

| 11,602,107 B2 | 3/2023 | Reeves et al. |
| 2015/0114519 A1 | 4/2015 | Hyde et al. |
| 2015/0272013 A1 | 10/2015 | Harada |
| 2022/0015311 A1 | 1/2022 | Reeves et al. |

FOREIGN PATENT DOCUMENTS

| CN | 105706897 A | 6/2016 |
| CN | 105981594 A | 10/2016 |
| CN | 107371830 A | 11/2017 |

(Continued)

OTHER PUBLICATIONS

Muzik et al.; Further Studies on the Grafting of Monocotyledonous Plants; American Journal of Botany (1954) vol. 41; pp. 448-455.*

(Continued)

*Primary Examiner* — Kent L Bell
(74) *Attorney, Agent, or Firm* — MORRISON & FOERSTER LLP (57) ABSTRACT

The invention relates to the grafting of perennial monocots such as bananas and oil palms. Processes for the production of such plants are disclosed herein.

26 Claims, 9 Drawing Sheets

(56) References Cited

FOREIGN PATENT DOCUMENTS

CN 108668663 A 10/2018

OTHER PUBLICATIONS

Muzik et al.; The Grafting of Large Monocotyledonous Plants; Science; 1952; 116:589-591.*
Andrews et al., (1993). "Graft incompatibility," Hort. Rev., 15:183-232.
Calderini, (1846). "Essai d'expériences sur la graffe des graminées," Ann. Sci.Nat. Bot., 6:131-133, 4 pages. English Translation.
Chung et al., (2007). "Rootstocks for grafting," Horticulture in Korea. Korean Society for Horticultural Science, 162-167.
Dransfield et al., (2008). "Genera Palmarum: the evolution and classification of palms," Royal Botanic Gardens, Kew, 745 pages.
Katayama et al., (1996). "Phylogenetic affinities of the grasses to other monocots as revealed by molecular analysis of chloroplast DNA," Current Genetics, 29:572-581.
King et al., (2008). "Grafting for Disease Resistance," HortScience, 43(6):1673-1676.
Kumar, (2011). "Propagation of plants by grafting and budding," Revised Edition. Washington: Horticultural and Landscape Architecture, Washington State University, 18 pages.
Lee et al., (2010). "Current status of vegetable grafting: Diffusion, grafting techniques, automation," Scientia Horticulturae, 127:93-105.
Lee, (1994). "Cultivation of Grafted Vegetables I. Current Status, Grafting Methods, and Benefits," HortScience, 29(4):235-239.
Louws et al., (2010). "Grafting fruiting vegetables to manage soilborne pathogens, foliar pathogens, arthropods and weeds," Scientia Horticulturae, 127:127-146.
Melnyk et al., (2015). "Plant grafting," Current Biology, 25(5):R183-R188.
Melnyk, (2017). "Plant grafting: insights into tissue regeneration," Regeneration, 4:3-14.
Mudge et al., (2009). "A history of grafting," Horticultural reviews, 35:437-493.
Muzik et al., (1952). "The Grafting of Large Monocotyledonous Plants," Science, 116:589-591.
Muzik et al., (1954). "Further studies on the grafting of monocotyledonous plants," American Journal of Botany, 41:448-455.
Obolensky, (1960). "Grafting of plant embryos and the use of ultrasonics," Qualitas plantarum et materiae vegetabiles, 7:273-288, 32 pages.
Schwarz et al., (2010). "Grafting as a tool to improve tolerance of vegetables to abiotic stresses: Thermal stress, water stress and organic pollutants," Scientia Horticulturae, 127:162-171.
Trias-Blasi et al., (2015). "A genus-level phylogenetic linear sequence of monocots," Taxon, 64(3):552-581.
Turnbull, (2010). "Grafting as a research tool," Plant Developmental Biology, 655:11-26.
Van Nocker et al., (2014). "Breeding better cultivars, faster: applications of new technologies for the rapid deployment of superior horticultural tree crops," Horticulture Research, 1:22, 8 pages.
Wang et al., (2017). "Plant grafting: how genetic exchange promotes vascular reconnection," New Phytologist, 214:56-65.
Zeevaart, (2008). "Leaf-produced floral signals," Current opinion in plant biology, 11:541-547.
Baulcombe, (2005). "RNA silencing," TRENDS in Biochemical Sciences, 30(6):290-293.
Bock, (2010). "The give-and-take of DNA: horizontal gene transfer in plants," Trends in Plant Science, 15(1):11-22.
Calarco et al., (2012). "Reprogramming of DNA methylation in pollen guides epigenetic inheritance via small RNA," Cell, 151(1):194-205.
Fuentes et al., (2014). "Horizontal genome transfer as an asexual path to the formation of new species," Nature, 511(7508):232-5, 15 pages.
Harada, (2010). "Grafting and RNA transport via phloem tissue in horticultural plants," Scientia Horticulturae, 125:545-550.
Kanehira et a., (2010). "Apple phloem cells contain some mRNAs transported over long distances," Tree Genetics & Genomes, 6:635-642.
Laurie, (1989). "The frequency of fertilization in wheat x pearl millet crosses," Genome, 32:1063-1067.
Stegemann et al., (2009). "Exchange of Genetic Material Between Cells in Plant Tissue Grafts," Science, 324:649-651.
Brosnan et al., (2007). "Nuclear gene silencing directs reception of long-distance mRNA silencing in *Arabidopsis*," PNAS USA, 104:14741-14746.
Goldschmidt, (2014). "Plant grafting: new mechanisms, evolutionary implications," Frontiers in Plant Sci., 5, 727.
Liu et al., (2006). "Screening for High-Temperature Tolerant Cotton Cultivars by Testing In Vitro Pollen Germination, Pollen Tube Growth and Boll Retention," Journal of Integrative Plant Biology, 48:706-714.
Molnar et al., (2010). "Small Silencing RNAs in Plants Are Mobile and Direct Epigenetic Modification in Recipient Cells," Science, 328:872-875.
Rouphael et al., (2017). "Grafting as a tool for tolerance of abiotic stress," Vegetable Grafting: Principles and Practices. Eds., pp. 171-215.
Sachs, (1949). "Vegetative Hybridization," Nature, 164:1009-1010.
Sachs, (1951). "Vegetative hybridization' in the tomato," Nature, 167:282-283.
Stubbe, (1954). "Über die vegetative Hybridisierung von Pflanzen," Die Kulturpflanze, 2:185-236, 56 pages. English Abstract.
Topoleski et al., (1963). "A study of graft-induced alterations in eggplant," Proc. Am. Soc. Hortic. Sci., 83:559-570.
Tournier et al., (2006). "Phloem flow strongly influences the systemic spread of silencing in GFP Nicotiana benthamiana plants," Plant Journal, 47:383-394.
Wu et al., (2013). "Inter-Species Grafting Caused Extensive and Heritable Alterations of DNA Methylation in Solanaceae Plants," PLoS ONE, 8:e61995, 11 pages.
Xu et al., (2013). "siRNA-mediated DNA methylation and H3K9 dimethylation in plants," Protein & Cell, 4:656-663.

\* cited by examiner

| Grafted species | No. fused[†] | No. attempts | Success rate |
|---|---|---|---|
| Banana – banana[‡] | 14 | 53 | 26 % |
| Oil palm – oil palm[§] | 2 | 6 | 33 % |

[†] Grafted plants were physically pulled apart with forceps to determine whether fusion occurred.

[‡] Banana grafts were formed from cultivated 'Cavendish' scions and wild *M. acuminata* rootstocks.

[§] Oil palm grafts were formed from different *E. guineensis* individuals of the same variety.

| Grafted species | No. fused[1] | No. attempts | Success rate |
|---|---|---|---|
| Date palm - date palm[2] | 6 | 45 | 13 % |

[1]Grafted plants were gently pulled with forceps to determine whether fusion occurred.
[2]Grafts were formed from different individuals of the same species.

| Grafted species | No. fused[1] | No. attempts | Success rate |
|---|---|---|---|
| Wheat - Sorghum | 9 | 19 | 47.4 % |

[1]Grafted plants were gently pulled with forceps to determine whether fusion occurred.

PERENNIAL MONOCOTYLEDON GRAFTING

CROSS REFERENCE TO RELATED APPLICATIONS

This application is a national stage application under 35 U.S.C. § 371 of International Application No. PCT/GB2019/053232, filed internationally on Nov. 14, 2019, which claims the benefit of priority of Great Britain Application No. 1818578.5, filed on Nov. 14, 2018, each of which are hereby incorporated by reference in their entireties.

FIELD OF THE INVENTION

The invention relates to the grafting of perennial monocotyledons such as bananas and oil palms.

BACKGROUND OF THE INVENTION

Grafting is the horticultural practice of fusing two plants so that they grow as one. Nearly all perennial orchard crops and ornamentals (i.e., apple, cherry, pecan, grape, rose, olive, citrus, maple, etc.) as well as many high-value crop species are grafted commercially (Hartmann et el., 2010).

It is believed that the first use of plant grafting was for clonal propagation of desirable plant varieties (Mudge et al., 2009). For example, many orchard species are highly heterozygous, which means the traits of the parents will segregate in subsequent generations. Therefore, growth from seeds is not a viable way to maintain desirable genotypes. Moreover, certain tree species, such as apple (*Malus* sp.), are difficult to propagate by rooting cuttings. Instead, branches of a superior tree can be grafted to stocks of alternative accessions to produce clones.

Grafting can serve to improve certain characteristics, including disease resistance and the ability to adapt to extreme temperatures or to edaphic factors, such as salt tolerance (Lee, 1994; Louws et al., 2010; Schwarz et al., 2010). In many cases, a disease resistant rootstock is able to confer protection against soil borne pathogens when grafted to a susceptible scion (King et al., 2008). Thus, grafting can help increase the overall yield of the plant. For example, grafted melons yield 25-55% more than non-grafts (Lee et al., 2010), and a 51-54% increase in yield was observed when rootstocks 'Helper' and 'Kagemusia' were used in tomato grafts (Chung and Lee, 2007).

Grafting also enables one plant to be supported by multiple root systems or one root system to support multiple plants as branches. This can speed the growth of an individual scion or allow the propagation of multiple scions to conserve space. This is particularly useful in orchard crop breeding. Lastly, by grafting a juvenile F1 hybrid seedling onto a mature rootstock, the hybrid may reach flowering many years sooner than if it had grown without grafting (Nocker and Gardiner, 2014).

Almost all reports of grafting specifically refer to dicotyledonous plant species, and in some cases gymnosperms or magnoliids. Successful grafting of monocotyledons is thought to be precluded because they lack vascular cambium tissue in their stems. Indeed, current consensus in the literature is that grafting monocotyledons is not possible (Melnyk, 2017b; J. Wang et al., 2017; Melnyk and Meyerowitz, 2015; Kumar, 2011; Hyde et al., 2015; Turnbull, 2010; Zeevaart, 2008; Andrews and Marquez, 1993).

Moreover, compared with the numerous reports of dicotyledonous grafting that span millennia, there are very few articles that claim monocotyledon grafting (Obolensky, 1960; Muzik and La Rue, 1952; Muzik and La Rue, 1954; Calderini, 1846). These reports lack a disclosure of the underlying methods (Calderini, 1846), were based on grafting mature internodes once plants were flowering (Muzik and La Rue, 1952; Muzik and La Rue, 1954), or involved placing embryos from one accession next to the endosperm of another or a section from one embryo between the radicle and plumule of another embryo, or a combination of these two approaches (Obolensky 1960). Muzik and La Rue (1952, 1954), while having convincing evidence for successful graft unions between monocotyledons, grafted at internodes, stem junctions between leaf offshoots, of the plants. Internodes form in monocotyledons later into adulthood, and thus internode grafting precludes grafting in the seedling stage. This complicates the procedure and reduces the benefits of the scion/rootstock combination in the adult plant. Their success rates were also very low, on average 3% and grafting flowering plants at internodes does not provide any commercial benefit. Moreover, germinating an embryo from a foreign endosperm does not generate a graft, and placing a section of embryo between the radicle and plumule results in a plant with genetically identical roots and shoots. These reports are mostly confined to grass species (Poaceae), while Muzik and La Rue (1954) grafted vine species in the monocot order Alismatales. The consensus among the scientific community is that, seemingly because of the structure of their vascular bundles, monocots cannot be grafted.

SUMMARY OF THE INVENTION

The present invention derives from the finding that perennial monocotyledonous plants are in fact amenable to grafting. Grafts between such monocots can be made between individuals of the same or different taxa, e.g. between individuals of the same variety or cultivar, between different varieties or cultivars of the same species, or between different species. These grafts can be performed in several monocotyledon families which are phylogenetically separated by many millions of years (Katayama and Ogihara, 1996; Soltis et al., 2018; Trias-Blasi et al., 2015), which implies that grafting within the monocotyledons is not restricted to specific families.

Disclosed herein are low-cost and rapid methods for grafting perennial monocots, including important crop species such as oil palm and banana. Grafting cultivated banana or oil palm scions to closely related stocks with complementary characteristics could alleviate many problems faced by these crops, such as the control of disease. Panama Disease tropical race 4 (TR4), a serious disease of banana, and *Ganoderma* sp., a serious disease of oil palm, are soil-borne. Thus, it is expected that a disease resistant rootstock will confer sufficient pseudoresistance to these pathogens, which has been reported in many other crops previously (King et al., 2008).

The invention provides a method of producing a grafted perennial monocot plant, comprising:
(a) providing a rootstock source comprising mesocotyl and radicle tissue of a first perennial monocot plant;
(b) providing a scion source comprising mesocotyl and plumule tissue of a second, different perennial monocot plant;
(c) placing said rootstock source in contact with said scion source such that said rootstock and scion sources are fused;

(d) allowing fusion of rootstock and scion sources such that functional vascular connections form between the rootstock and scion sources; and generating a grafted perennial monocot plant from said fused rootstock and scion sources.

The invention further provides a grafted perennial monocot plant comprising functional vascular connections between the rootstock source and the scion source.

Yet further provided by the invention is a method of producing a chimeric perennial monocot plant, comprising:
 (a) providing a laterally sectioned first seed comprising mesocotyl tissue or a laterally sectioned first bulb comprising basal plate tissue, wherein the seed or bulb is from a first perennial monocot plant;
 (b) providing a laterally sectioned second seed comprising mesocotyl tissue or a laterally sectioned second bulb comprising basal plate tissue, wherein the seed or bulb is from a second perennial monocot plant;
 (c) placing said laterally sectioned first and second seeds or said laterally sectioned first and second bulbs into contact so that they are fused;
 (d) allowing fusion of said laterally sectioned first and second seeds or said laterally sectioned first and second bulbs; and
 (e) generating a chimeric perennial monocot plant from said fused laterally sectioned first and second seeds or said laterally sectioned first and second bulbs.

The invention further provides a method comprising propagating the chimeric perennial monocot plant of step (e) of the method of producing a chimeric perennial monocot plant as above, preferably to generate a further perennial monocot plant that is a chimera between the first and second plants of steps (a) and (b) of the method of producing a chimeric perennial monocot plant as above.

Yet further provided by the invention is a chimeric perennial monocot plant comprising tissues derived from fused first and second laterally sectioned seeds or bulbs.

BRIEF DESCRIPTION OF THE DRAWINGS

FIGS. 2A-2B. Schematics illustrating exchange of embryo parts between seeds to allow grafting of monocotyledons.

FIGS. 3A-3B. Grafts between perennial monocotyledons eight days following grafting.

FIGS. 5A-5B. Banana grafts form vascular reconnections.

FIGS. 6A-6B. Grafting date palm (*Phoenix dactylifera*).

FIGS. 7A-7C. Method of producing graft chimeras from seeds.

FIGS. 8A-8B. Grafts and chimeras made between bulbous monocots.

DETAILED DESCRIPTION OF THE INVENTION

Definitions

Accession: A unique variety of a plant species.

Annual: A plant that completes its lifecycle, from germination to producing seeds, in one year.

Basal plate: A meristematic tissue found in bulbous monocotyledons that separates the shoot from the root in the bulb and forms new tissues of the plant.

Biennial: A plant that completes its lifecycle, from germination to producing seeds, in two years.

Callus: Undifferentiated plant cells regenerating in tissue culture; proliferating tissue at the graft junction to re-connect the vasculature.

Chimera: A plant with tissues containing separate genotypes.

Dicotyledon, commonly referred to as a dicot: A flowering plant that typically contains two embryonic leaves in the seed, reticulate veins, and a taproot root system. Examples of dicots include many agronomic and horticultural plants, such as tomato, carrot, apple, oak, and soybean.

Endosperm: A tissue inside plant seeds that stores nutritious energy, in the form of starch, oil or protein, for the embryo.

Embryo: An immature plant, which has rudimentary tissue for the leaves, roots and stems. In flowering plants, the embryo is a part of the seed.

Germination: The process by which a plant embryo begins to sprout and grow into a seedling.

Graft: The union of two plants so they grow as one (See Scion and Rootstock).

Graft, to: (v.) To place plant parts together to fuse them.

Hybrid: A first filial generation (F1) plant derived from two genetically different parents.

Interspecific: between to different/separate species.

Intraspecific: within the same species.

Junction: The contact zone where the scion meets the rootstock in a grafted plant.

Mesocotyl: The tissue between the shoot (plumule) and root (radicle). In most monocots, the mesocotyl can be easily found because it is directly below the epiblast, which is a flap-like projection on the exterior of the embryo.

Micropropagation: A tissue culture method for cloning plants on nutrient media, usually indefinitely.

Monocotyledon, commonly referred to as Monocot: A flowering plant that typically contains one embryonic leaf in the seed, parallel veins, and a fibrous root system. Examples of monocots include many agronomic crops and ornamental plants, such as all cereals (i.e., maize, wheat, rice), banana, palm, orchids, lilies, and tulips.

Monocotyledonous: (adj.) of a monocotyledon.

Perennial: A plant that lives longer than two years.

Plumule: The embryonic shoot or leaves of a plant. In monocots, the plumule includes the coleoptile, embryonic leaves and shoot apical meristem.

Radicle: The embryonic root system of a plant. In monocots, the radicle is covered by the coleorhiza, a protective sheath.

Regeneration: A process of growing an adult plant from a single cell. Usually, this involves growing plants in tissue culture with hormones to proliferate and differentiate organs.

Rootstock: The root-bearing portion of a grafted plant.

Selectable marker: A nucleic acid sequence whose expression allows identification of plants containing the nucleic acid sequence.

Scion: The shoot-bearing portion of a grafted plant.

Tissue culture: A set of techniques that can be used to grow plants, plant cells, plant tissues, and organs in aseptic conditions on nutrient medium. Use of plant hormones can be used to regenerate adult plants from individual plant cells.

Plant Choice

To initiate the process, two plants are chosen for grafting. Any two plants that are closely related can be used. Grafting is preferably carried out between plants of the same genus, but can be performed between plants of the same family or order. Grafting can be carried out between plants of different species but of the same genus. Grafting can also be carried out between plants of different species but of the same family. Grafting can further be carried out between plants of different species but of the same order. Grafting can be carried out between plants of the same species but of a different genotype. Grafting can also be carried out between plants of the same species but of a different accession. Grafting can further be carried out between plants of the same species but of a different cultivar. Grafting can yet further be carried out between plants of the same species but of a different variety.

Preferably, the plants being grafted are perennial monocots. Perennial monocots include lilioid monocots. Lilioid monocots can be from an order selected from Petrosaviales, Dioscoreales, Pandanales, Liliales and Asparagales. Perennial monocots also include commelinid monocots. Commelinid monocots can be from an order selected from Arecales, Zingiberales, Poales and Commelinales. Perennial monocots include crop plants and ornamental plants.

Crop plants and ornamental plants that are perennial monocots include bananas and plantains (Musaceae) such as *Musa acuminata, Musa balbisiana*, and autotriploid *Musa acuminata* 'Cavendish' and 'Gros Michel'. Cultivated bananas are infertile autotriploids (AAA) derived from the progenitor species *Musa acuminata* (genome AA). Additionally, plantains (AAB or ABB) are infertile interspecific allotriploids derived from the hybridisation of *M. acuminata* (AA) and *Musa balbisiana* (genome BB). The triploid nature of cultivated banana and plantain prevents them from producing viable seeds, whereas wild species are diploid and can produce viable seeds.

Crop plants and ornamental plants that are perennial monocots also include palms (Arecaceae). Palms include, for example, oil palm (*Elaeis* sp.), date palm (*Pheonix* sp.), queen palm (*Syagrus* sp), coconut (*Cocos nucifera*), areca palm (*Chrysalidocarpus lutescens*), Bismarck palm (*Bismarckia nobilis*), bottle palm (*Hyophorbe lagenicaulis*), carpentaria palm (*Carpentaria acuminata*), Chinese fan palm (*Livistona chinensis*), kentia palm (*Howea forsteriana*), lady palm (*Rhapis excelsa*), lipstick palm (*Cyrtostachys renda*), Mexican fan palm (*Washingtonia robusta*), royal palm (*Roystonea oleracea*), saw palmetto palm (*Serenoa repens*) and windmill palm (*Trachycarpus fortunei*). Oil palm is propagated by seed, as it does not produce pups (clonal offshoots) (Dransfield et al., 2008).

Crop plants and ornamental plants that are perennial monocots also include orchids (Orchidaceae). Orchids include, for example, vanilla (*Vanilla planifolia*), *Phalaenopsis* sp., *Cymbinium* sp., *Dendrobium* sp., *Cambria* sp., *Vanda* sp. or *Cattleya* sp. Crop plants and ornamental plants that are perennial monocots also include, for example, bamboos (Babusaea), sugarcanes (*Saccharum* sp.), agave (*Agave tequilana*), ginger (*Zingiber officinale*), turmeric (*Curcuma longa*), cardamom (*Elettaria cardamomum*), asparagus (*Asparagus officinalis*), pineapple (*Ananas comosus*) and water chestnut (*Eleocharis dulcis*).

Crop plants and ornamental plants that are perennial monocots also include bulbous plants. Bulbous plants include, for example, *Agapanthus, Allium, Alstroemeria, Amaryllis, Arum, Asphodelus, Calochortus, Camassia, Canna, Colchicum, Convallaria, Crinum, Crocosmia, Crocus, Dierama, Eucomis, Freesia, Fritillaria, Galanthus, Galtonia, Gladiolus, Gloriosa, Haemanthus, Hyacinthus, Hymenocallis, Hippeastrum, Iris, Ixia, Leucojum, Lilium, Muscari, Narcissus, Nerine, Ornithogalum, Pancratium, Paradisea, Polianthes, Scilla, Sprekelia, Sternbergia, Trillium, Tritonia, Tulipa, Watsonia, Zantedeschia*, and *Zephyranthes*.

Seed Sterilisation

For the best results, grafting should be performed in aseptic conditions. Seeds of both plants are obtained and can be surface-sterilised. Preferably, the seeds are mature, but immature seeds can also be used. Any suitable sterilisation methodology may be used. In cereals, for example, seeds can be sterilised in 1-4% (v/v) sodium hypochlorite solution with 0.01% (v/v) Tween-20 or a similar surfactant for 25-45 minutes. The solution can be washed completely by several rinses of sterile water. In banana, oil palm and date palm, seeds can be, for example, sterilised in 2-4% (v/v) Plant Preservative Mixture™ (PPM™, Apollo Scientific, UK) overnight or longer. PPM™ can be used to sterilise all monocotyledonous seeds and can be added in media (0.1-1% v/v) to greatly reduce contamination.

Partial Seed Germination

Germination of seeds can be initiated by any suitable method. In cereals, for example, the seeds can be soaked for 12-35 hours in sterile water between 20-30° C. in darkness. If PPM™ is used as the sterilisation agent, then the seeds may be kept in this solution during the germination phase. Soaking the seeds causes water absorption, which eases subsequent grafting steps. Soaking may be carried out for any suitable time period. Alternatively, dry seeds can be used. In perennial monocots, for example banana and palm, seeds can for example be soaked for 3 days between 28-30° C. in darkness in a gibberellic acid ($GA_3$) solution, where the first day is a mixture of 2-4% (v/v) PPM™ for sterilization and $GA_3$. In banana, 0.0002-0.001% (w/v) $GA_3$ is generally sufficient to initiate germination. In oil palm and date palm, 0.01-0.1% (w/v) $GA_3$ is generally sufficient to initiate germination. Following partial germination, the plumule and radicle can be exchanged between different *Elaeis guineensis* individuals for grafting.

Grafting of the Plant Embryo

Seeds of the two plants are taken. The seed coat can be present or be removed. If the seed coat is removed, it may be removed by any means, such as with a razor blade. The seeds can be dry or imbibed. Where the seeds are imbibed, they are preferably imbibed in water. Where the seeds are imbibed in water, they are preferably imbibed in water for 8 to 72 hours. The seeds can instead or additionally be partially germinated in the dark. Where the seeds are partially germinated in the dark, they preferably partially germinated in the dark for 2 to 30 days. The two seeds are then cut. One seed will provide the material for the rootstock source comprising mesocotyl and radicle tissue, while the other seed will provide the material for the scion source comprising mesocotyl and plumule tissue.

In each seed, a transverse cut can be made across the mesocotyl, the differentiation point between the radicle and the plumule, inside the plant embryo. Greater success results from the thinnest blades, as the mesocotyl can be narrow. For example, a seed can be cut with a cutting edge with a thickness of 0.1 to 0.3 mm. The cut can be made with a blade, for example a razor blade. The cut can also be made with a tissue puncher. Preferably, a tissue puncher used for this purpose is 0.75 to 3.5 mm, most preferably 1.2 mm, in diameter. The scion source comprising mesocotyl and plumule tissue can be excised from both seeds and exchanged between seeds and can be pressed in close contact with the rootstock source comprising mesocotyl and radicle tissue. Optionally, an adhesive, grafting wax or a paste comprising soaked endosperm of the same grafting partner, can be applied to the edges of the graft junction to keep the scion source and the rootstock source in adhesion. Care must be taken to prevent the glue or other adhesive from seeping into the junction between the scion source and rootstock source.

Alternatively, a hole puncher, preferably with a diameter of 1-1.25 mm, fitted with a plunger can instead be used to exchange embryonic pieces from dry or imbibed seeds. The bottom of the sharpened edge of the puncher can be placed over the epiblast of the seed comprising the material for the rootstock source comprising mesocotyl and radicle tissue. Gentle movement downward can then cut a hole into the seed to the endosperm which bisects the mesocotyl. The shoot can then be excised, and ejected by the plunger. Subsequently, the scion source of another seed can be removed in the same manner, yet can be ejected into the hole bored into the first seed to align the two halves of the mesocotyl such that they are in direct contact with each other. An exact fit of embryo pieces is usually accomplished by this method as the diameter of the cut piece is determined by the diameter of the puncher. Aided by a puncher, a skilled technician can graft 60-100 plants per hour. When carefully grafted, embryo pieces demonstrate complete fusion between 18-42% of the time, depending on the combination.

Irrespective of the method used, the grafted seed is then typically kept in a moist/humid environment, usually on wet sterile filter paper, for 2-7 days or longer for slower growing species until fusion occurs between the rootstock and scion sources. Fusion means that functional vascular connections form between the rootstock and scion sources. Preferably, the fusion step comprises growing the fused rootstock and scion sources on nitrocellulose membrane. For example, the grafted seed can be kept at a temperature of 20 to 28° C. in the dark for 2 to 4 days before exposure to light for 7 days. The graft seedling can then optionally be transferred to soil under normal growing conditions.

Grafting Via Shoot Transplantation

Grafting can be performed on newly germinated seedlings. Germination can proceed in darkness until the plumule is 0.5-1 cm in length. Darkness tends to cause mesocotyl elongation which aids the process. The shoot can be cut in the shape of a wedge or circle at the epiblast and placed into a different seed which has had its plumule excised in the same manner. This approach is particularly useful for larger seeds, or when aiming to graft a shoot from a species that is infertile, and so not able to make seeds, onto an incipient root rootstock of a fertile recipient.

Grafting in Tissue Culture

Monocot grafting can also be performed on plant tissue regenerated in tissue culture. This can be applied to any suitable species, but is particularly applicable to bananas and plantains. Unlike most plants, cultivated banana is infertile and as such lacks the ability to form seeds. This makes it impossible to obtain embryos from seeds. Instead, newly formed banana shoots can be micropropagated in tissue culture and then grafted to desirable rootstocks that have been micropropagated or isolated from embryos. Banana plants are typically kept on nutrient media containing 6-Benzylaminopurine (BAP), an artificial cytokinin plant hormone, to continually proliferate shoots. If BAP is removed, then the shoots typically begin to form roots. Exploiting this, cultivated bananas can be grafted to desirable rootstocks. Banana shoots on BAP media can be excised and dissected to keep a single shoot connected to callus tissue from where they regenerate. These can constitute the scion source of the graft. Likewise, wild banana callus tissue (or embryonic roots from a germinated seed) can serve as the rootstock source. A callus of the same diameter which lacks a shoot is typically pressed in close contact to the wounded callus of the scion callus and transferred to media without BAP. The period during which graft fusion occurs also allows differentiation from the bottom callus to derive the root system. Via this method, banana plants can be generated within 5 to 20 days.

To graft cultivated (infertile) banana with wild banana, wild *M. acuminata* or *M. balbisiana* banana seeds can be germinated to obtain small seedlings to serve as a rootstock source. Subsequent dissection at the mesocotyl can separate the root system from the shoot of these wild bananas. Then, shoots of cultivated banana ('Cavendish') can be generated in tissue culture to serve as the scion source. The root system of wild *M. acuminata* can be taken and placed in contact with the shoot, for example of 'Cavendish' or 'Gros Michel' and allowed to fuse.

Vasculature Reconnection Testing

The presence of functional vascular connections between the rootstock source and the scion source can be assessed. For example, the assessing can comprise pulling the rootstock source and the scion source apart, wherein resistance indicates the presence of functional vascular connections between the rootstock and scion sources. Alternatively or additionally, a tracking dye can be added to the rootstock source and the scion source observed. The presence of tracking dye in the scion source then indicates the presence of functional vascular connections (i.e., xylem) between the rootstock and scion sources. Moreover, a tracking dye can be added to the scion source and the rootstock source observed. The presence of tracking dye in the rootstock source then indicates the presence of functional vascular connections (i.e., phloem) between the rootstock and scion sources. Preferably, the tracking dye can be carboxyfluorescein diacetate (CFDA).

Chimeric Plant Production

Chimeric plants can be produced in annual and perennial monocots via the methods provided here. This is accomplished by sectioning either seeds or bulbs laterally and realigning the sides at the mesocotyl, root-shoot-junction, or basal plate (for bulbs), and attaching these together. In the case of two seeds or bulbs, the seeds or bulbs are laterally bisected. The attachment can be with physical means or using an adhesive. Physical means of holding the bulb parts together include but are not limited to the use of tapes, parafilm, rubber bands or other bands, clamps, compostable bag strips, clips, ties and pins. Adhesive means of holding the bulb parts together include but are not limited to glues, pastes, and wax. Subsequent germination yields the graft chimera. Typically, two plants will make up the chimera. Optionally, more than two plants, for example three or four plants, can make up the chimera.

The chimeric plant can then be propagated. In general, this will entail propagation from tissue containing cells derived from all of the plants that make up the chimera, such that the resultant plant is also chimeric. Chimeric perennial monocot plants can be propagated by cloning meristematic tissue possessing a conglomeration of two (or more) constituents, either by cuttings or offshoots, by more grafting (e.g. of chimeric branches or tissues), or by producing meristematic tissue in tissue culture to make clones (e.g. in banana or orchids). Chimeric bulbous perennial monocot plants can be propagated by side bulbs from the grafted bulb.

EXAMPLES

Example 1—Palm Grafting

Seeds of each palm accession were surface sterilized. In the case of some palms (e.g., oil palm), the outer operculum (a husk-like covering over the seed) was removed with a table vice. Not all palm seeds possess an operculum (e.g., date palm). Seeds were imbibed in sterile water containing 0.01-0.1% (w/v) gibberellic acid ($GA_3$) at 28° C. on a shaker in darkness for 72 hours. The solution was refreshed each day. Gibberellic acid serves to accelerate the germination process. Seeds were then placed on moist filter paper in 9 cm diameter petri plates sealed with micropore tape and kept in darkness at 28° C. Palm seeds were kept in these conditions until germination had proceeded such that the embryonic shoot (plumule) and root (radicle) had emerged from the seed.

When shoots were 5-20 mm in length, they were cut with a 0.1-0.3 mm razor blade at the interface between the shoot and root (mesocotyl). Rootstocks were obtained in the same manner by cutting the interface between the root and shoot (mesocotyl) with a 0.1-0.3 mm thick razor blade. Excised shoot and rootstocks were then grafted together immediately after cutting. Fine forceps were used to manipulate the tissues such that the wounded edge of the scion matches that of the rootstock. These edges were pressed together.

Glue or grafting wax was applied to the graft site to maintain adhesion until the union between scion and rootstock fused (it usually takes 14 days for fusion to occur). Care was taken to prevent the glue or wax from seeping between or into the junction. This was accomplished by holding the scion and rootstock together with forceps until the glue or wax set (usually about 10 seconds).

Grafted palms were then placed onto moist filter paper or tissue culture media consisting of 4.41 $g \cdot L^{-1}$ Murashige and Skoog salts, 10 $g \cdot L^{-1}$ sucrose, 6.5 $g \cdot L^{-1}$ phytagel (pH 5.8) in 9 cm diameter petri plates with tall lids, and maintained in a photoperiod of 16 hours light, 8 hours dark. Light intensity was 80 μmol photons $m^{-2} \cdot s^{-1}$ and temperature maintained at 28° C. After about 14 days the graft junction was formed and plants were transferred to soil.

Example 2—Banana Grafting

Cultivated banana is infertile and so lacks seeds. It was therefore not possible to obtain embryos and the component parts required for grafting directly. However, young banana shoots formed during micropropagation in tissue culture were compatible with grafting to rootstocks that are derived from embryos of other species, or to rootstocks obtained from micropropagation in tissue culture.

To obtain shoots suitable for grafting, banana plants (e.g., *Musa acuminata* 'Cavendish') were placed on Banana Shoot Multiplication (BSM) media consisting of 4.41 $g \cdot L^{-1}$ Murashige and Skoog salts, 30 $g \cdot L^{-1}$ sucrose, 100 $mg \cdot L^{-1}$ ascorbic acid, 6.5 $g \cdot L^{-1}$ phytagel and 2.25 $mg \cdot L^{-1}$ $N^6$-benzyladenine (BAP) an artificial cytokinin plant hormone, (pH 5.8) in 9 cm diameter dishes, and sealed with parafilm. Photoperiod was maintained at 16 hours light, 8 hours dark, with a light intensity of 80 μmol photons $m^{-2} \cdot s^{-1}$. Temperature was maintained at 28° C. Under these conditions, explants continually generated shoots. Other cytokinins might be suitable to micropropagate banana in tissue culture. In addition to BAP, a greater number of cytokinins are available. These include kinetin, zeatin, dihydrozeatin, thidiazuron (TDZ), diphenylurea, 6-Benzylamino-9-(2-tetrahydropyranyl)-9H-purine (BPA), Forchlorfenuron, and $N^6$-Isopentenyladenine (2iP). The preferred working concentration for cytokinins ranges between 0.01 to 20 $mg \cdot L^{-1}$.

When shoots were 5-20 mm in length, they were cut with a razor blade at the interface between the shoot and callus in tissue culture and immediately grafted to a rootstock. Rootstocks could either be obtained by removing BAP from the above media for 14 days, and then cutting the interface between the root and shoot (mesocotyl) with a 0.1-0.3 mm thick razor blade, or by removing a section of mesocotyl and root from a fertile banana or similar species. In both cases, the shoot and rootstocks were then grafted together immediately after cutting. Fine forceps were used to manipulate the tissue such that the wounded edge of the scion matches that of the rootstock. These edges were pressed together.

Glue or grafting wax could optionally be applied to the graft site to maintain adhesion until the union between scion and rootstock fuse (it usually takes 14 days for fusion to occur). Care then had to be taken to prevent the glue or wax from seeping between or into the junction. This was accomplished by holding the scion and rootstock together with forceps until the glue or wax set (usually about 10 seconds).

Grafted bananas were then placed onto moist filter paper or tissue culture media consisting of 4.41 $g \cdot L^{-1}$ Murashige and Skoog salts, 10 $g \cdot L^{-1}$ sucrose, 6.5 $g \cdot L^{-1}$ phytagel (pH 5.8) in 9 cm diameter petri plates with tall lids, and maintained in a photoperiod of 16 hours light, 8 hours dark. Light intensity was 80 μmol photons $m^{-2} \cdot s^{-1}$ and temperature maintained at 28° C. After about 14 days the graft junction was formed and plants were transferred to soil.

Example 3—Perennial Grass Grafting

Seeds of each grass accession were surface sterilized. They could then either be imbibed in water overnight (8-35 hours) or left dry. A tissue puncher with a 1-1.5 mm (for example 1.2 mm) diameter and 0.1-0.3 mm thick cutting edge was used to bore out the entire plumule and half of the mesocotyl. The mesocotyl was bisected such that half of it is still connected with the plumule and the remaining half is still connected to the radicle of the imbibed seed. The incision was made directly through the seed coat (i.e., the seed coat is not removed beforehand). A 0.1-0.3 mm thick razor/scalpel blade can be used as an alternative tool to excise the plumule.

The removed plumule was replaced by one from a different seed (either from the same or different species), which can either be dry or imbibed. Dry plumule inserts appeared to absorb water from the imbibed seed causing them to swell, and this generated firm contact with the mesocotyl of the inserted plumule (scion source) and the radical in the seed (rootstock source) to form graft unions.

In an alternative method, seeds were transversely cut through at the mesocotyl to separate the plumule from the radicle, and to bisect the endosperm. Cut seeds of separate accessions of the same or different plant species were then re-aligned and pressed together. The seeds then germinated into fused plants. In this method, the endosperms of each accession were also placed into close contact and served to support the germination of the radicle or plumule.

Irrespective of the methods used, the grafts were allowed to germinate on nitrocellulose membranes placed on top of moist filter paper in petri plates with tall lids in darkness at 20-28° C. The membrane prevented roots from becoming embedded into the filter paper, and tall lids reduced the chance of graft junctions being forced apart once the shoot elongated to press against the lid.

After incubation in darkness for two to four days, the seeds were exposed to light. A period of darkness following graft fusion encourages mesocotyl elongation and thus led to better fusion and a greater degree of success. Once graft fusion occurred, typically after 7 days, they were transferred to tissue culture conditions or to soil.

Example 4—Intraspecific Grafting of Banana for Disease Resistance

Banana (*Musa* sp.) is the most valuable fruit in the world. As cultivated banana is infertile (lacks seeds), it must be clonally propagated and relatively few cultivated varieties are in large-scale production. The most prevalent variety of banana is 'Cavendish' which replaced 'Gros Michel' following the outbreak of Tropical Race-1 (TR1) of Panama Disease caused by the soil borne fungal pathogen, *Fusarium oxysporum*, in the 1950s to 1960s. Currently Tropical Race-4 (TR4) threatens global banana production, as 'Cavendish' is susceptible.

Grafting is utilized as a tool for conferring disease resistance to crops through fusion of a susceptible scion with a resistant rootstock, thus demonstrating that banana can be grafted, including 'Cavendish' to TR4 resistant wild banana accessions. This result develops an immediate and promising solution to control Panama Disease in banana. It may also be possible for the 'Gros Michel' variety to be re-established via this approach. It is conceivable that there are a great number of additional benefits that may be conferred to banana through grafting different rootstocks.

Example 5—Vasculature Reconnection Tests

Figure 1:
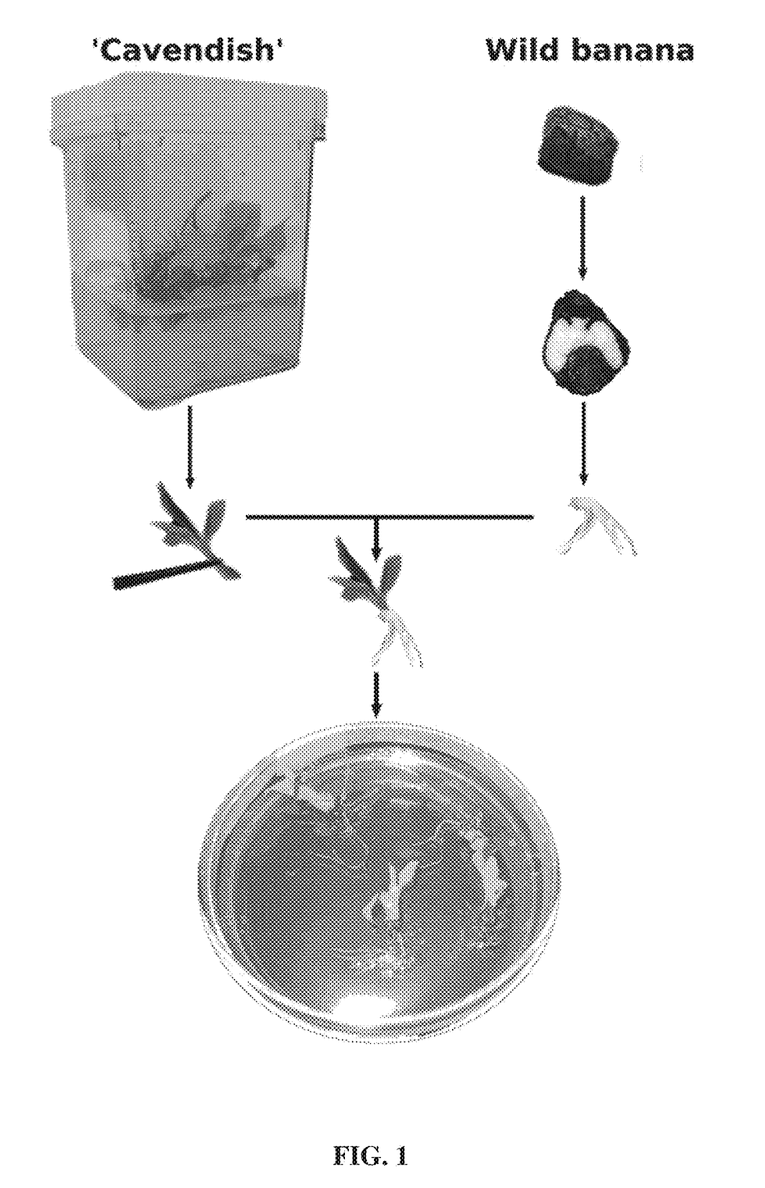
FIG. 1. A schematic for grafting cultivated banana (i.e., 'Cavendish') to disease resistant wild banana.
Figure 2A:
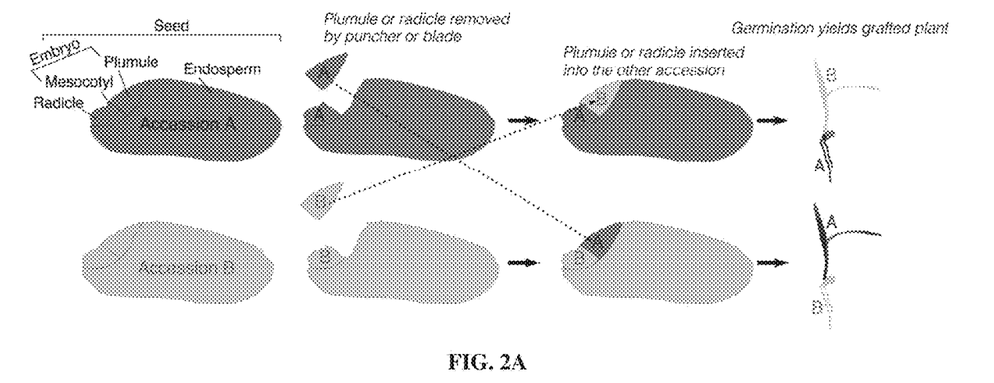
FIG. 2A. The plumule is removed with a blade or tissue puncher from two different accessions. These are then placed into the corresponding gap introduced into the seed of the other accession. After this exchange, seeds are allowed to germinate and generate fused plants, or grafts.
Figure 2B:
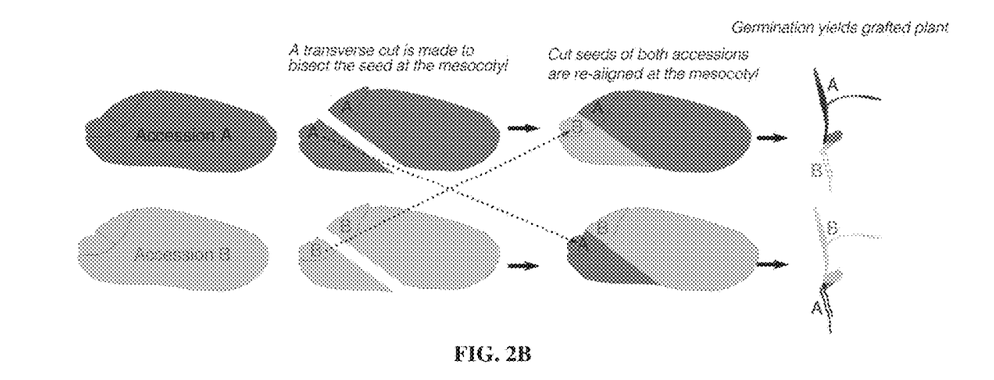
FIG. 2B. This exchange can also be performed by transversely cutting through the seed at the mesocotyl to separate the plumule from the radicle. Cut seeds of separate accessions of the same or different plant species can then be re-aligned and pressed together. The seed germinates into a fused plant. This method differs slightly from a) in that both endosperms of each accession are also placed into close contact and may serve to support the respective germination of the radicle or plumule better.
Figure 3A:
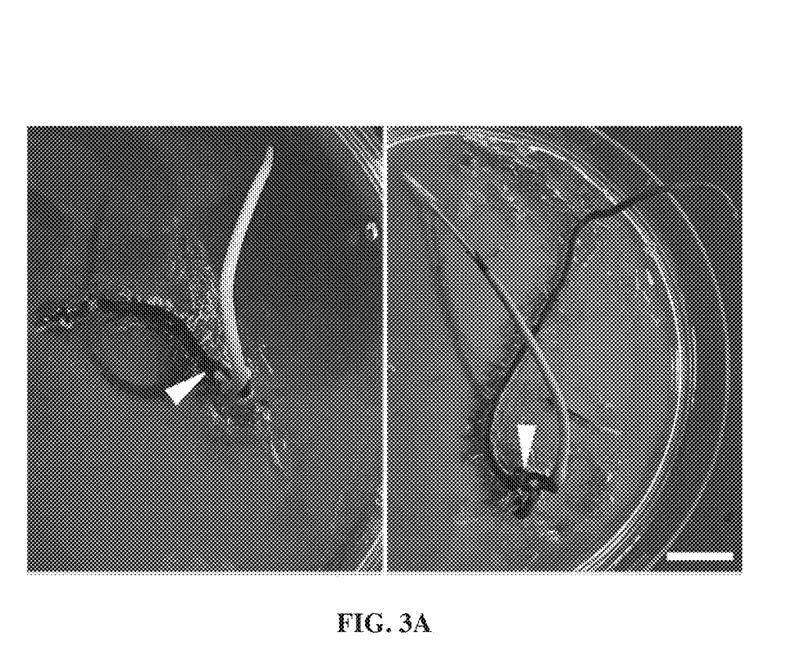
FIG. 3A. Representative images of two different intraspecific grafts between oil palm (*Elaeis guineensis*), FIG. 3B. Representative images of two different intraspecific banana grafts between *Musa acuminata* 'Cavendish' (AAA) scions and wild *Musa acuminata* (AA) rootstocks. Arrowheads point to the graft junctions. Scale-bars represent 1 cm.
Figure 3B:
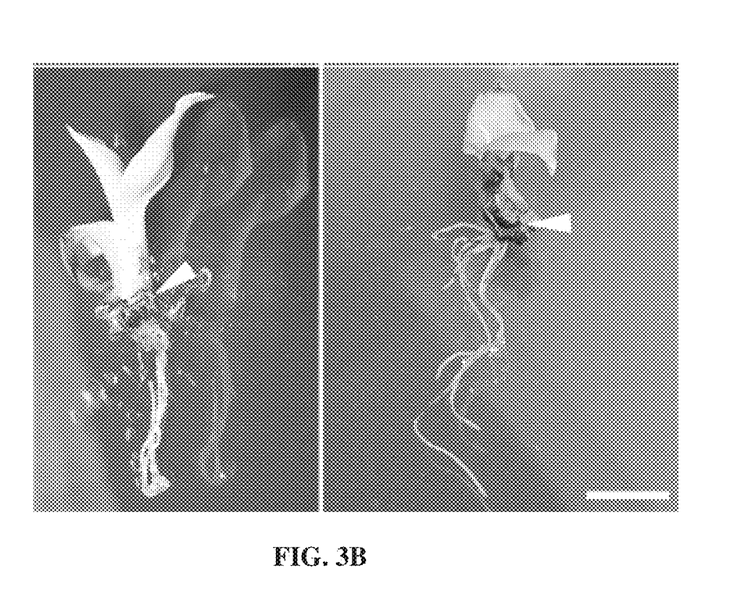
Figure 4:
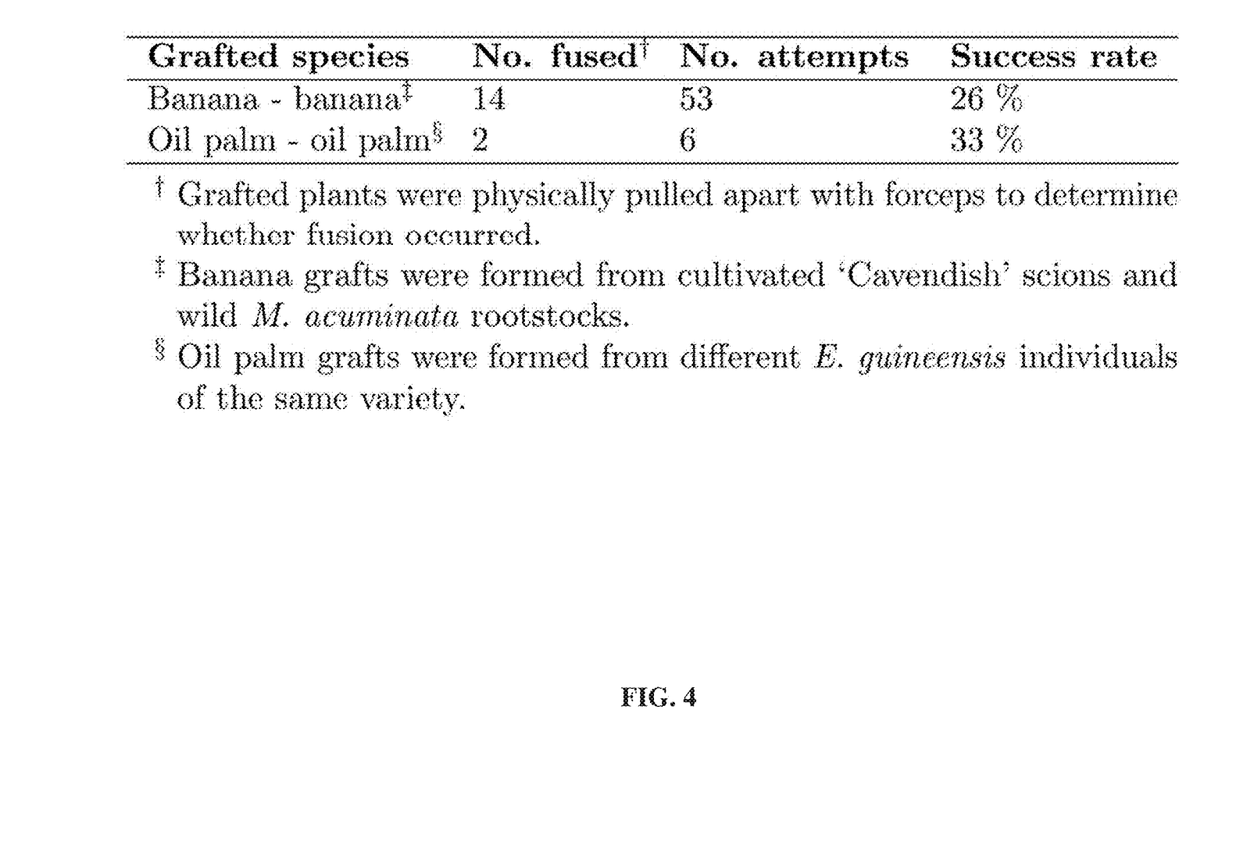
FIG. 4. Results for perennial monocotyledons (banana and oil palm).

After two weeks, it was attempted to pull grafted banana and oil palm intraspecific grafts apart, with strong resistance indicating graft fusion. If there was strong resistance, then the graft was considered to be fused. Intraspecific grafts between cultivated banana 'Cavendish' and its wild progenitor *M. acuminata* demonstrated a 26% (n=53) fusion rate (See FIG. 4). Likewise, intervarietal oil palm grafts were fused 33% (n=6) (See FIG. 4). Thus, this indicated that monocotyledon grafting was possible in economically important perennial monocotyledonous crops. Moreover, this indicated that grafting is possible across three distantly related monocotyledonous taxa (grasses, bananas and palms).

Figure 5A:
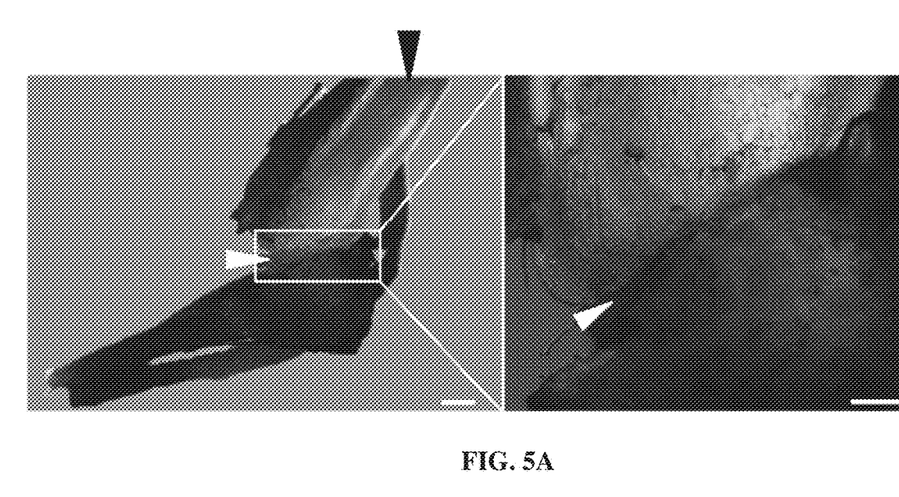
FIG. 5A. A transverse section of a grafted banana plant. A fluorescent dye crosses the graft junction from the shoot into the rootstock indicating phloem connection. Panels to the left and right show the tissue under low and high magnification, respectively.
Figure 5B:
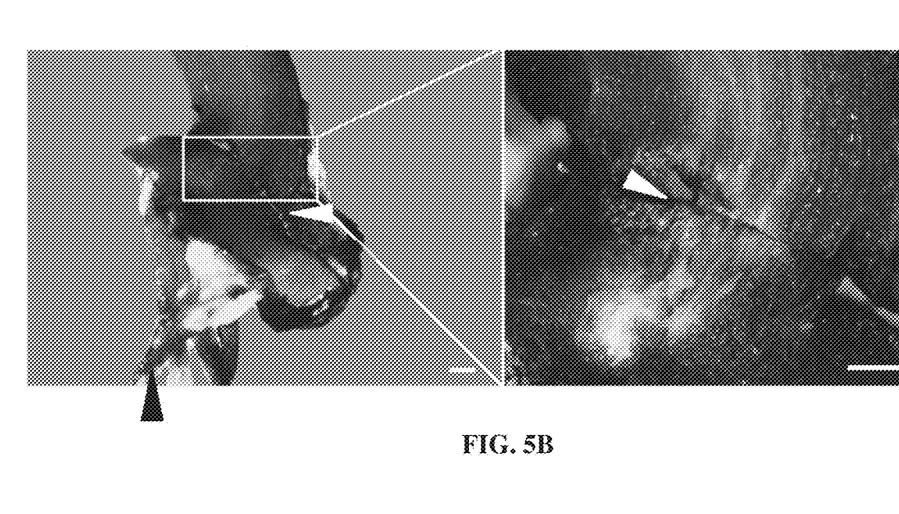
FIG. 5B. A fluorescent dye crosses the graft junction from the rootstock into the scion indicating xylem connection. Panels to the left and right show the tissue under low and high magnification, respectively. White arrows indicate the graft junctions and black arrows indicate the site where the fluorescent dye was applied. All plants are 2 weeks old. Scale-bars represent 1 cm.
Figure 6A:
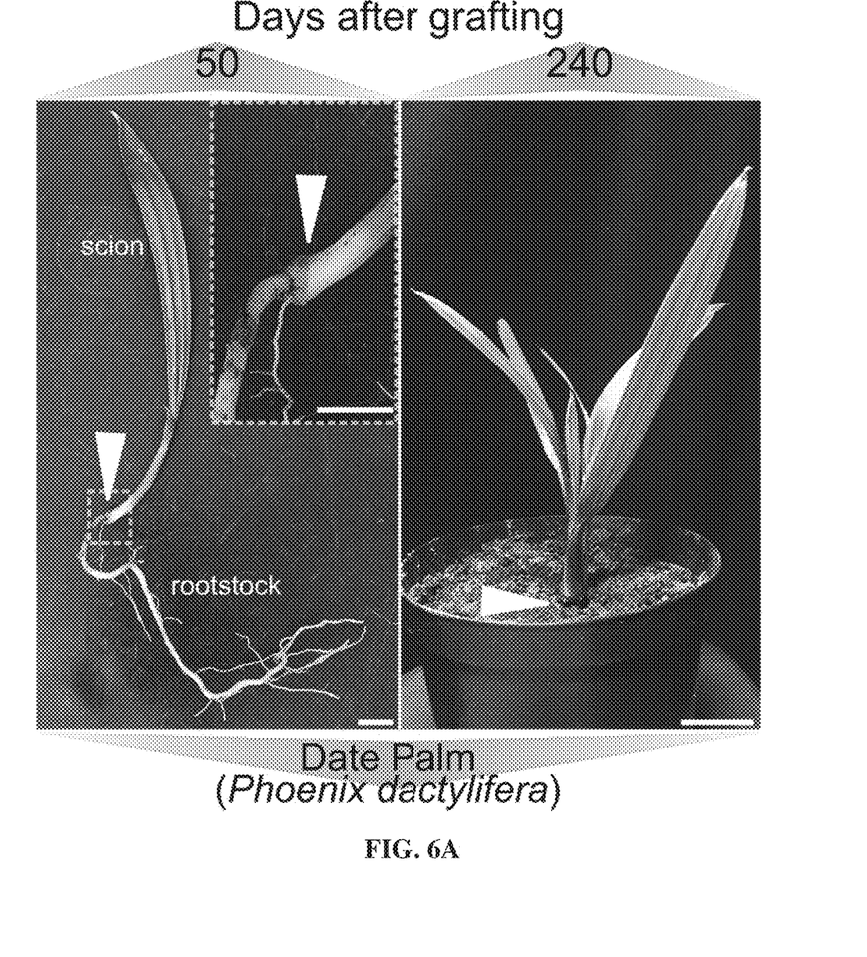
FIG. 6A. An image of an intraspecific date palm graft 50 days after grafting (left panel) with an enlarged view of the graft junction in the upper right corner, and 240 days after grafting in soil (right panel). Arrowheads point to the graft junctions. Scale-bars represent 1 cm (left panel) and 5 cm (right panel).
Figure 6B:
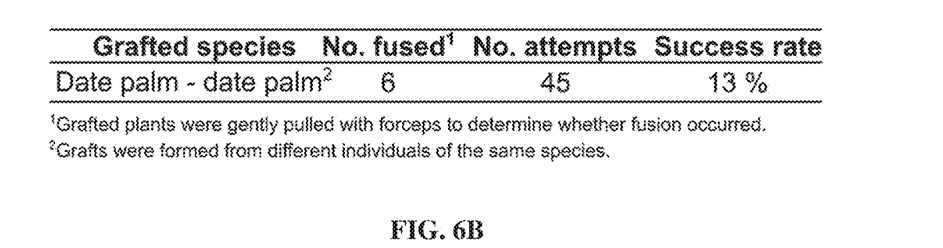
FIG. 6B. Grafting rates for date palm grown in soil two weeks after grafting.
Figure 7A:
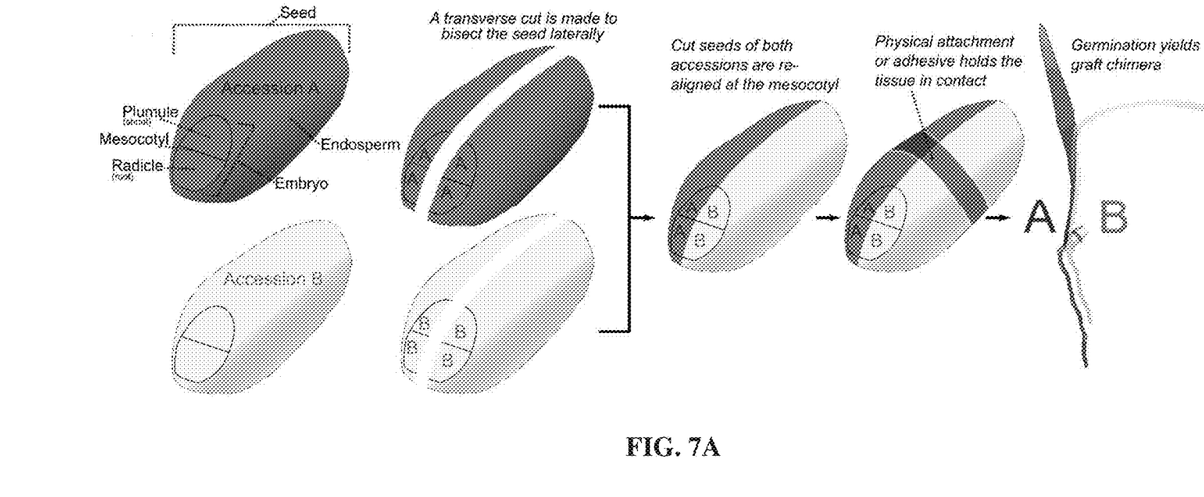
FIG. 7A. A schematic for producing chimeric plants by grafting seeds.
Figure 7B:
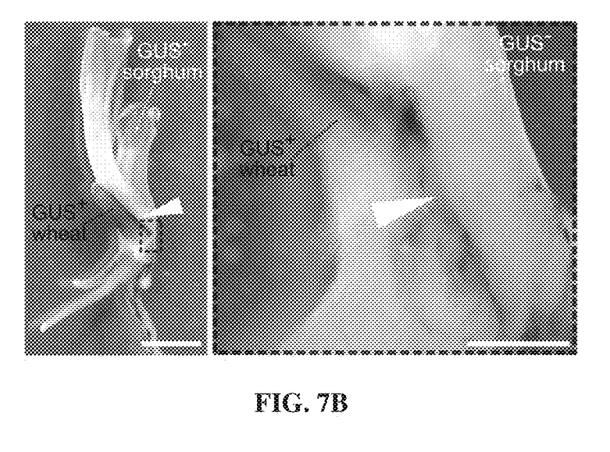
FIG. 7B. Representative image of an interspecific graft chimera between a GUS gene containing wheat (*Triticum aestivum*) accession and GUS negative sorghum (*Sorghum bicolor*). Representative image of a 1 week old chimera is shown to the right after staining—a darker colour shows GUS positive tissue. A section through the fused tissue is shown to the left. Arrowheads point to the graft junction.
Figure 7C:
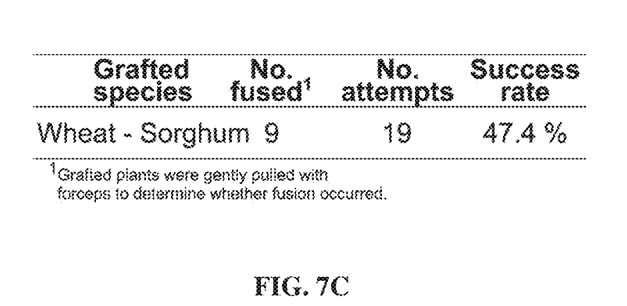
FIG. 7C. Results for forming chimeras from grafting in wheat and sorghum. Scale-bars represent 1 cm (b, right) and 1 mm (b, left).
Figure 8A:
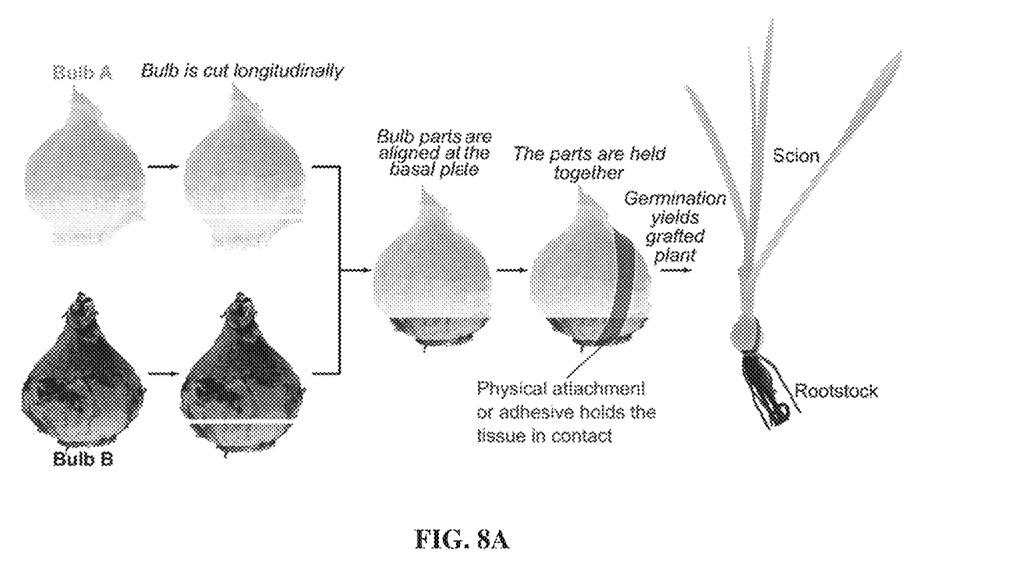
FIG. 8A. A schematic for forming grafts in bulbs.
Figure 8B:
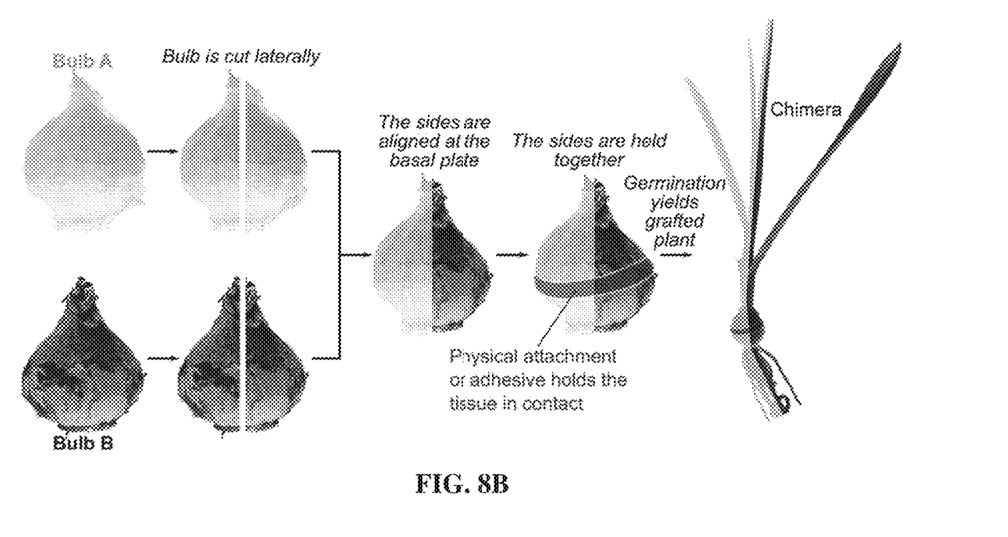
FIG. 8B. A schematic for forming chimeras from grafting bulbs.

Further tests for functionality of vascular reconnections were carried out, with fully reconnected vasculature being a criterion for compatible grafts. After eight days, intraspecific grafts between 'Cavendish' and wild *M. acuminata* were evaluated. When carboxyfluorescein diacetate (CFDA) dye was applied to the rootstock of banana grafts, fluorescence was observed in the scion after approximately 50 minutes (see FIGS. 5A-5B). This indicated that CFDA traveled through the transpiration stream in these banana grafts and therefore that vascular (i.e., xylem) connectivity had formed. CFDA was also applied to the scion approximately 2 cm above the junction. Within one hour, fluorescence was visible in the root system (see FIGS. 5A-5B). This demonstrated that CFDA had traveled in the phloem and therefore indicated functional phloem connections transverse the graft junction.

BIBLIOGRAPHY

Andrews, P. K. and C. S. Marquez (1993) Graft incompatibility. *Hort. Rev.* 15, 183-232.
Calderini, I. M. (1846) Essai d'expériences sur la graffe des graminées. *Ann. Sci. Nat. Bot. III*, 131-133.
Chung, H. D. and J.-M. Lee (2007) Rootstocks for grafting. *Korean Society for Horticultural Science*, 162-167.
Dransfield, J., N. W. Uhl and Kew Royal Botanic Gardens (2008) Genera Palmarum: the evolution and classification of palms. Kew Pub, 732.
Hartmann, H. T., D. E. Kester, F. T. J. Davies and R. L. Geneve (2010) Plant propagation: principles and practices. 8th. Prentice Hall/Pearson, 928.
Hyde, R. A., M. Y. Ishikawa, R. C. Petroski, D. B. Tuckerman, T. A. Weaver, V. Y. H. Wood and L. L. Wood (2015). Harvesting and grafting of trees. U.S. patent application Ser. No. 14/069,079

Katayama, H. and Y. Ogihara (1996) Phylogenetic affinities of the grasses to other monocots as revealed by molecular analysis of chloroplast DNA. *Current Genetics* 29, 572-581.

King, S. R., A. R. Davis, W. Liu and A. Levi (2008) Grafting for Disease Resistance. *HortScience* 43, 1673-1676.

Kumar, G. N. M. (2011) Propagation of plants by grafting and budding, *Revised Edition. Washington: Horticultural and Landscape Architecture, Washington State University*, 16.

Lee, J.-M. (1994). Cultivation of Grafted Vegetables I. Current Status, Grafting Methods, and Benefits. *HortScience* 29, 235-239.

Lee, J.-M., C. Kubota, S. J. Tsao, Z. Bie, P. Hoyos Echevarria, L. Morra and M. Oda G A Honorary (2010) Current status of vegetable grafting: Diffusion, grafting techniques, automation. *Scientia Horticulturae* 127, 93-105.

Louws, F. J., C. L. Rivard and C. Kubota (2010) Grafting fruiting vegetables to manage soilborne pathogens, foliar pathogens, arthropods and weeds. *Scientia Horticulturae* 127, 127-146.

Melnyk, C. W. and E. M. Meyerowitz (2015) Plant grafting. *Current Biology* 25, 183-188.

Melnyk, C. W. (2017b). Plant grafting: insights into tissue regeneration. *Regeneration* 4, 3-14.

Mudge, K., J. Janick, S. Scofield and E. E. Goldschmidt (2009) A history of grafting. *Horticultural reviews* 35, 437-493.

Muzik, T. J. and C. D. La Rue (1952) The Grafting of Large Monocotyledonous Plants. *Science* 116, 589-591.

Muzik, T. J. and C. D. La Rue (1954) Further studies on the grafting of monocotyledonous plants. *American Journal of Botany*, 448-455.

Nocker, S. van and S. E. Gardiner (2014) Breeding better cultivars, faster: applications of new technologies for the rapid deployment of superior horticultural tree crops. *Horticulture Research* 1, 14022.

Obolensky, G. (1960) Grafting of plant embryos and the use of ultrasonics. *Qualitas plantarum et materiae vegetabiles* 7, 273-288.

Schwarz, D., Y. Rouphael and J. H. Venema (2010) Grafting as a tool to improve tolerance of vegetables to abiotic stresses: Thermal stress, water stress and organic pollutants. *Scientia Horticulturae* 127, 162-171.

Soltis, D. E., P. S. Soltis, P. K. Endress, M. W. Chase, S. R. Manchester, W. S. Judd, L. C. Majure and E. Mavrodiev (2018). Phylogeny and evolution of the angiosperms. *University of Chicago Press*, 580.

Trias-Blasi, A., W. J. Baker, A. L. Haigh, D. A. Simpson, O. Weber and P. Wilkin (2015) A genus-level phylogenetic linear sequence of monocots. *Taxon* 64, 552-581.

Turnbull, C. G. N. (2010) Grafting as a research tool. *Plant Developmental Biology*. Springer, 11-26.

Wang, J., L. Jiang and R. Wu (2017) Plant grafting: how genetic exchange promotes vascular reconnection. *New Phytologist* 214, 56-65.

Zeevaart, J. A. D. (2008) Leaf-produced floral signals. *Current opinion in plant biology* 11, 541-547.

The invention claimed is:

1. A method of producing a grafted perennial monocot plant, comprising:
   (a) providing a rootstock source comprising mesocotyl and radicle tissue of a first perennial monocot plant;
   (b) providing a scion source comprising mesocotyl and plumule tissue of a second, different perennial monocot plant;
   (c) placing said rootstock source in contact with said scion source such that said rootstock and scion sources are fused;
   (d) allowing fusion of rootstock and scion sources such that functional vascular connections form between the rootstock and scion sources; and
   (e) generating a grafted perennial monocot plant from said fused rootstock and scion sources.

2. The method of claim 1, wherein said first and second perennial monocot plants are both:
   (i) commelinid monocots; or
   (ii) lilioid monocots.

3. The method of claim 1, wherein the fusion between the rootstock source and the scion source is stable over the lifespan of the grafted perennial monocot plant.

4. The method of claim 1, wherein:
   (i) step (c) comprises applying one or more of: a paste comprising soaked endosperm of the same perennial monocot species, an adhesive, and grafting wax at the contact between said rootstock source and said scion source;
   (ii) step (d) comprises growing the fused rootstock and scion sources on nitrocellulose membrane; and/or
   (iii) step (e) comprises generating the grafted perennial monocot plant in tissue culture or on soil.

5. The method of claim 1, wherein the method further comprises:
   (i) a step of surface sterilising the rootstock source and/or the scion source prior to step (a); and/or
   (ii) assessing the presence of functional vascular connections between the rootstock source and the scion source after step (d).

6. The method of claim 5, wherein the assessing comprises:
   (i) pulling the rootstock source and the scion source apart, wherein resistance indicates the presence of functional vascular connections between the rootstock and scion sources; or
   (ii) applying a tracking dye to the rootstock source and observing the scion source, wherein the presence of tracking dye in the scion source indicates the presence of functional vascular connections between the rootstock and scion sources.

7. The method of claim 1, wherein the scion source is obtained by micropropagation in tissue culture and the rootstock source is obtained from embryonic tissue and/or obtained by micropropagation in tissue culture.

8. The method of claim 7, wherein the embryonic tissue is obtained from a seed.

9. The method of claim 8, wherein the seed is cut with a cutting edge with a thickness of 0.1 to 0.3 mm.

10. The method of claim 7, wherein the scion source is micropropagated on nutrient medium containing a cytokinin.

11. The method of claim 1 wherein the rootstock source and the scion source are from a perennial monocot plant of:
    (i) the same species; or
    (ii) a different species within the same order.

12. The method of claim 1, wherein the perennial monocot plant is a banana or plantain (Musaceae).

13. The method of claim 12, wherein the grafted banana or plantain plant is generated within 5 to 20 days.

14. A grafted perennial monocot plant comprising functional vascular connections between the rootstock source and the scion source, wherein the grafted perennial monocot plant is produced by the method of claim 1.

15. The grafted perennial monocot plant of claim 14, wherein the rootstock source and the scion source are from a perennial monocot plant of:
   (i) the same species; or
   (ii) a different species within the same order.

16. The grafted perennial monocot plant of claim 14, wherein the perennial monocot plant is a banana or plantain (Musaceae).

17. The method of claim 1, wherein the scion source and the rootstock source are obtained from:
   (i) a first embryonic tissue and a second embryonic tissue;
   (ii) by micropropagation in tissue culture; and/or
   (iii) a first bulb and a second bulb.

18. The method of claim 17, wherein the first and second bulbs are transversely cut.

19. The method of claim 17, wherein:
   (A) said first and second embryonic tissues are obtained from a first seed and a second seed, and said first and second seeds:
      (i) comprise their seed coats;
      (ii) are dry or imbibed in water; and/or
      (iii) are partially germinated in the dark; or
   (B) said first seed is imbibed in water; preferably for 8 to 72 hours; and said second seed is dry;
before the first and second embryonic tissues are obtained from said first and second seeds.

20. The method of claim 17, wherein the first and second seeds are:
   (i) transversely cut; or
   (ii) cut with a tissue puncher.

21. The method of claim 17, wherein the scion source is tissue cultured on nutrient medium containing a cytokinin.

22. The method of claim 17, wherein the rootstock source and the scion source are from a perennial monocot plant of:
   (i) the same species; or
   (ii) a different species within the same order.

23. The method of claim 17, wherein the perennial monocot plant is a crop plant or an ornamental plant.

24. The grafted perennial monocot plant of claim 14, wherein the perennial monocot plant is a crop plant or an ornamental plant.

25. The grafted perennial monocot plant of claim 24, wherein the perennial monocot plant is:
   (i) a palm (Arecaceae);
   (ii) an orchid (Orchidaceae);
   (iii) a bamboo (Babusaea), a sugarcane (*Saccharum* sp.), agave (*Agave tequilana*), ginger (*Zingiber officinale*), turmeric (*Curcuma longa*), cardamom (*Elettaria cardamomum*), asparagus (*Asparagus officinalis*), pineapple (*Ananas comosus*), or water chestnut (*Eleocharis dulcis*); or
   (iv) a bulbous plant selected from Agapanthus, *Allium, Alstroemeria, Amaryllis, Arum, Asphodelus, Calochortus, Camassia, Canna, Colchicum, Convallaria, Crinum, Crocosmia, Crocus, Dierama, Eucomis, Freesia, Fritillaria, Galanthus, Galtonia, Gladiolus, Gloriosa, Haemanthus, Hyacinthus, Hymenocallis, Hippeastrum, Iris, Ixia, Leucojum, Lilium, Muscari, Narcissus, Nerine, Ornithogalum, Pancratium, Paradisea, Polianthes, Scilla, Sprekelia, Sternbergia, Trillium, Tritonia, Tulipa, Watsonia, Zantedeschia*, and *Zephyranthes*.

26. The method of claim 23, wherein the perennial monocot plant is:
   (i) a palm (Arecaceae);
   (ii) an orchid (Orchidaceae);
   (iii) a bamboo (Babusaea), a sugarcane (*Saccharum* sp.), agave (*Agave tequilana*), ginger (*Zingiber officinale*), turmeric (*Curcuma longa*), cardamom (*Elettaria cardamomum*), asparagus (*Asparagus officinalis*), pineapple (*Ananas comosus*), or water chestnut (*Eleocharis dulcis*); or
   (iv) a bulbous plant selected from Agapanthus, *Allium, Alstroemeria, Amaryllis, Arum, Asphodelus, Calochortus, Camassia, Canna, Colchicum, Convallaria, Crinum, Crocosmia, Crocus, Dierama, Eucomis, Freesia, Fritillaria, Galanthus, Galtonia, Gladiolus, Gloriosa, Haemanthus, Hyacinthus, Hymenocallis, Hippeastrum, Iris, Ixia, Leucojum, Lilium, Muscari, Narcissus, Nerine, Ornithogalum, Pancratium, Paradisea, Polianthes, Scilla, Sprekelia, Sternbergia, Trillium, Tritonia, Tulipa, Watsonia, Zantedeschia*, and *Zephyranthes*.

* * * * *